United States Patent
Qian et al.

(10) Patent No.: US 12,351,590 B2
(45) Date of Patent: Jul. 8, 2025

(54) PYRROLOPYRIMIDINE COMPOUND AND USE THEREOF

(71) Applicants: GUANGZHOU JOYO PHARMATECH CO., LTD., Guangdong (CN); MEDSHINE DISCOVERY INC., Jiangsu (CN)

(72) Inventors: Wenyuan Qian, Shanghai (CN); Changqing Wei, Shanghai (CN); Guoping Hu, Shanghai (CN); Jian Li, Shanghai (CN); Shuhui Chen, Shanghai (CN)

(73) Assignees: GUANGZHOU JOYO PHARMATECH CO., LTD., Guangdong (CN); MEDSHINE DISCOVERY INC., Jiangsu (CN)

( * ) Notice: Subject to any disclaimer, the term of this patent is extended or adjusted under 35 U.S.C. 154(b) by 847 days.

(21) Appl. No.: 17/596,151

(22) PCT Filed: Jun. 5, 2020

(86) PCT No.: PCT/CN2020/094534
§ 371 (c)(1),
(2) Date: Dec. 3, 2021

(87) PCT Pub. No.: WO2020/244614
PCT Pub. Date: Dec. 10, 2020

(65) Prior Publication Data
US 2022/0227788 A1    Jul. 21, 2022

(30) Foreign Application Priority Data
Jun. 5, 2019  (CN) .......................... 201910487056

(51) Int. Cl.
C07D 519/00    (2006.01)
A61P 19/02     (2006.01)

(52) U.S. Cl.
CPC ............ C07D 519/00 (2013.01); A61P 19/02 (2018.01)

(58) Field of Classification Search
CPC ............................... C07D 519/00; A61P 19/02
See application file for complete search history.

(56) References Cited

U.S. PATENT DOCUMENTS

| | | |
|---|---|---|
| 2007/0292430 A1 | 12/2007 | Blumenkopf et al. |
| 2017/0360794 A1 | 12/2017 | Wu et al. |
| 2018/0162879 A1 | 6/2018 | Wu et al. |
| 2022/0017522 A1 | 1/2022 | Liu et al. |

FOREIGN PATENT DOCUMENTS

| | | |
|---|---|---|
| CN | 107652308 A | 2/2018 |
| CN | 107805259 A | 3/2018 |
| JP | 2003516405 A | 5/2003 |
| JP | 2018516264 A | 6/2018 |
| JP | 2018199623 A | 12/2018 |
| WO | WO-2011137022 A1 | 11/2011 |
| WO | WO-2013085802 A1 | 6/2013 |
| WO | WO-2013088257 A1 | 6/2013 |
| WO | WO-2016116025 A1 | 7/2016 |
| WO | WO-2016192563 A1 | 12/2016 |
| WO | WO-2017143990 A1 | 8/2017 |

OTHER PUBLICATIONS

Lange et al, Bioisosteric Replacements of the Pyrazole Moiety of Rimonabant: Synthesis, Biological Properties, and Molecular Modeling Investigations of Thiazoles, Triazoles, and Imidazoles as Potent and Selective CB1 Cannabinoid Receptor Antagonists, J. Med. Chem, 2005, 48, 1823-1838 (Year: 2005).*

Jun. 20, 2023 Extended European Search Report issued in European Patent Application No. 20817895.4.

Jun. 22, 2023 First Office Action issued in Malaysian Patent Application No. PI2021007196.

Aug. 17, 2023 First Office Action issued in Eurasian Patent Application No. 202193249.

Jul. 24, 2023 First Office Action issued in Indonesian Patent Application No. P00202112387.

Database Chemcats [Online] Feb. 7, 2012 (Feb. 7, 2012), Aurora Building Blocks 7: "N-(5,6,7,8-tetrahydro-[1,2,4]triazolo[5, 1-f]pyridin-6-yl)-7H-pyrrolo[3,2-e]pyrimidin-4-amine", XP093052109.

Database Chemcats [Online] Jun. 7, 2012 (Jun. 7, 2012), Aurora Building Blocks 7: "[1,2,4]Triazolo[1,5-a]pyridin-6-amine, 5,6,7,8-tetrahydro-2-(1-methylethyi)-N-7H-pyrrolo[2,3-d]pyrimidin-4-yl-", XP093052105.

(Continued)

*Primary Examiner* — Noble E Jarrell
*Assistant Examiner* — Phillip Matthew Rzeczycki
(74) *Attorney, Agent, or Firm* — Harness, Dickey & Pierce, P.L.C.

(57) ABSTRACT

The present invention relates to a pyrrolopyrimidine compound used as a JAK inhibitor, and the use thereof in the preparation of a drug for treating a JAK1- and/or JAK2-associated disease, and in specifically relates to a compound represented by formula (I), an isomer thereof or a pharmaceutically acceptable salt thereof.

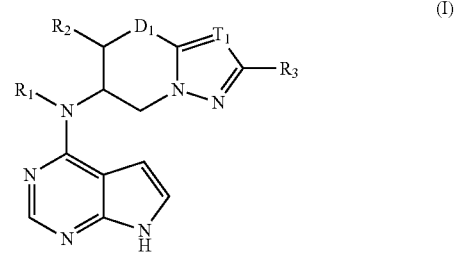

17 Claims, No Drawings

(56) References Cited

OTHER PUBLICATIONS

Jun. 22, 2022 First office action issued in Chinese Patent Application No. 2020800408137.
Jul. 1, 2022 First office action issued in Indian patent application No. 202117062034.
Jul. 31, 2020 International Search Report issued in International Patent Application No. PCT/CN2020/094534.
Jul. 31, 2020 Written Opinion of the International Searching Authority issued in International Patent Application No. PCT/CN2020/094534.
Vainchenker W.E T al.(2008).
John J.O'Shea, 2004, Nature Reviews Drug Discovery 3, 555-564.
Daniella M. Schwartz, 2017, Nature Reviews Drug Discovery 16, 843-862.
Apr. 1, 2024 First Office Action issued in Korean Patent Application No. 10-2022-7000127.
Jan. 12, 2023 First Office Action issued in Australian Patent Application No. 2020288567.
Jan. 5, 2023 First Office Action issued in Canadian Patent Application No. 3140467.
Dec. 20, 2022 First Office Action issued in Japanese Patent Application No. 2021571814.
5,6,7,8-tetrahydro-2-(1-methylethyl)-N-7H-pyrrolo[2,3-d]pyrimidin-4-yl-[1,2,4]triazolo[1,5-a]pyridin-6-amine and 5,6,7,8-tetrahydro-N-7H-pyrrolo[2,3-d]pyrimidin-4-yl-[1,2,4]triazolo[1,5-a]pyridin-6-amine were cited in Australian First office Action(AU2020288567). Year: 2012. 5,6,7,8-tetrahydro-2-(1-methylethyl)-N-7H-pyrrolo[2,3-d]pyrimidin-4-yl-[1,2,3]triazolo[1,5-a]pyridin-5-amine (CAS RN,1376247-73-2): Entered STN Jun. 7, 2012 5,6,7,8-tetrahydro-N-7H-pyrrolo[2,3-d]pyrimidin-4-yl-1[1,2,4]triazolo[1,5-a]pyridin-6-amine(CAS RN 1355699-51-2): Entered STN Feb. 7, 2012.
Jul. 30, 2024 First Office Action issued in Mexican Patent Application No. MX/A/2021/015056.
Dec. 17, 2024 Second Office Action issued in Korean Patent Application No. 10-2022-7000127.

* cited by examiner

PYRROLOPYRIMIDINE COMPOUND AND USE THEREOF

CROSS-REFERENCE TO RELATED APPLICATIONS

This application is a U.S. National Phase Application under 35 U.S.C. 371 of International Application No. PCT/CN2020/094534, filed on Jun. 5, 2020, which claims the benefit of Chinese Patent Application No. CN201910487056.7 filed on Jun. 5, 2019. The entire disclosures of the above applications are incorporated herein by reference.

TECHNICAL FIELD

The present disclosure relates to a pyrrolopyrimidine compound as a JAK inhibitor and use thereof in preparing a medicament for treating a JAK1- or/and JAK2-related disease, and in particular, to a compound represented by formula (I), an isomer thereof or a pharmaceutically acceptable salt thereof.

BACKGROUND

Janus kinases (JAKs) are a group of cytoplasmic tyrosine kinases that transmit cytokine signals from membrane receptors to STAT transcription factors. The JAK family includes four members, JAK1, JAK2, JAK3 and TYK2. The JAK-STAT pathway transmits extracellular signals from a variety of cytokines, growth factors and hormones to the nucleus and is responsible for the expression of thousands of protein-coding genes. The JAK-STAT pathway converting extracellular signals into transcriptional responses involves several steps: 1) The conformation of the cytokine receptors on the cell surface changes when they binds to their corresponding cytokine ligands, causing dimerization of the receptor molecules; the receptor-coupled JAK kinases are brought into close proximity with the dimerized receptors and activated through reciprocal tyrosine phosphorylation. 2) The activated JAKs catalyze the phosphorylation of tyrosine residues on the receptors; then the phosphorylated tyrosines and surrounding amino acid sequences form a docking site, and STAT proteins containing an SH2 domain are recruited to the docking site. 3) Finally, JAK kinases catalyze the phosphorylation of STAT proteins bound to the receptors; the activated STAT proteins leave the receptors and form dimers, which are then transferred into the nucleus to regulate the transcription of specific genes. JAK-STAT intracellular signal transduction serves interferons, most interleukins, and a variety of cytokines and endocrine factors, such as EPO, TPO, GH, OSM, LIF, CNTF, GM-CSF and PRL (Vainchenker W. et at. (2008)).

JAK-1, JAK-2 and TYK-2 are expressed in various tissue cells in humans, while JAK-3 is mainly expressed in various hematopoietic cells, mainly including bone marrow cells, thymocytes, NK cells, and activated B and T lymphocytes. JAK1 can bind to IL-10, IL-19, IL-20, IL-22, IL-26, IL-28, IFN-α, IFN-γ, IL-6 in the gp130 family, and other receptors containing γc. JAK1 has become a novel target in disease-related fields such as immunity, inflammation and cancer. JAK2 plays an important role in the regulation of a variety of receptor signals including EPO, GH, PRL, IFN-γ, and IL-3, IL-5 and GM-CSF in the βc family. A base mutation in the JAK2 gene in humans JAK2 V617F, is closely related to the development of polycythemia vera (PV), essential thrombocythemia (ET), idiopathic myelofibrosis (IMF), chronic myelogenous leukemia (CML), and the like in myeloproliferative diseases. JAK3 regulates cell signaling by binding to the common γ-chain (γc) in cytokine receptor complexes such as IL-2, IL-4, IL-7, IL-9, IL-15 and IL-21. Either JAK3 or γc mutations can cause severe combined immunodeficiency. Abnormal JAK3 activity manifests as remarkable decreases in T cells and NK cells and loss of B cell function, and may seriously affect normal biological functions of the immune system and the like. Based on its functional characteristics and special tissue distribution, JAK3 has become an attractive therapeutic target for immune system-related diseases. TYK2 is the $1^{st}$ member of the JAK family, which can be activated by a variety of receptors including IFNs, IL-10, IL-6, IL-12, IL-23 and IL-27. In mice, the loss of TYK2 function causes defects in the signaling pathways of various cytokine receptors, leading to viral infection, compromised antibacterial immune functions, and increased risks of pulmonary infection, etc. (John J. O'Shea, 2004, *Nature Reviews Drug Discovery* 3, 555-564). Different JAK family members selectively bind to different cytokine receptors and confer signaling specificity to exert different physiological function. This selective manner allows relatively specific applications of JAK inhibitors in treating diseases. For example, the IL-2 or IL-4 receptor, along with the common γ chain, binds to JAK1 and JAK3, while the type I receptor having the same β chain binds to JAK2. The type I receptor using gp130 (glycoprotein 130) and the type I receptor activated by heterodimeric cytokines preferentially bind to JAK1/2 and TYK2. The type I receptor activated by hormone-like cytokines binds to and activates JAK2 kinase. The type II receptor for interferon binds to JAK1 and TYK2, while the receptor for the IL-10 cytokine family binds to JAK1/2 and TYK2. The specific bindings of the above cytokines and their receptors to JAK family members trigger different physiological effects, providing the possibility for the treatment of different diseases. Heterodimerization of JAK1 with other JAKs transduces cytokine-driven pro-inflammatory signaling. Therefore, inhibition of JAK1 and/or other JAKs is expected to have therapeutic benefit for a range of inflammatory conditions and other diseases driven by JAK-mediated signal transduction (Daniella M. Schwartz, 2017, *Nature Reviews Drug Discovery* 16, 843-862.)

CONTENT OF THE PRESENT INVENTION

The present invention provides a compound represented by formula (I), an isomer thereof or a pharmaceutically acceptable salt thereof,

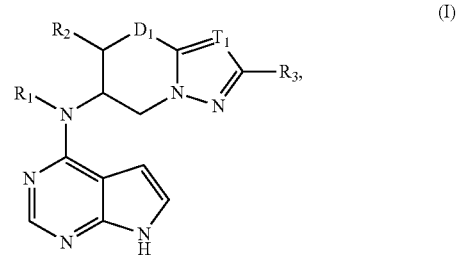

wherein,
$T_1$ is CH or N;
$D_1$ is a single bond, O or $CH_2$;

$R_1$ is H or $C_{1-3}$ alkyl, the $C_{1-3}$ alkyl is optionally substituted with 1, 2 or 3 $R_a$;

$R_2$ is H or $C_{1-3}$ alkyl, the $C_{1-3}$ alkyl is optionally substituted with 1, 2 or 3 $R_b$;

$R_3$ is selected from H, F, Cl, Br, I, CN and $C_{1-3}$ alkyl, the $C_{1-3}$ alkyl is optionally substituted with 1, 2 or 3 $R_c$;

$R_a$, $R_b$, and $R_c$ are each independently selected from F, Cl, Br, I and $NH_2$.

In some embodiments of the present invention, $R_1$ is H or $CH_3$; the other variables are as defined herein.

In some embodiments of the present invention, $R_2$ is H or $CH_3$; the other variables are as defined herein.

In some embodiments of the present invention, $R_3$ is selected from H, F, Cl, Br, I and CN; the other variables are as defined herein.

In some embodiments of the present invention, $R_3$ is selected from CN.

In some embodiments of the present invention, for the compound, the isomer thereof or the pharmaceutically acceptable salt thereof, the compound is selected from:

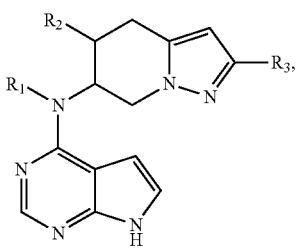

(I-1)

wherein $R_1$, $R_2$ and $R_3$ are as defined herein.

Some other embodiments of the present invention are derived from any combination of the variables as described above.

The present invention further provides a compound of the following formulas, an isomer thereof or a pharmaceutically acceptable salt thereof:

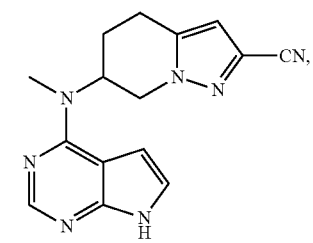

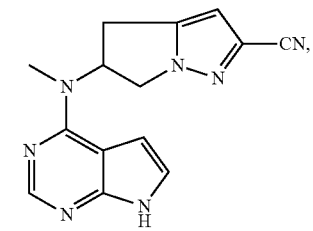

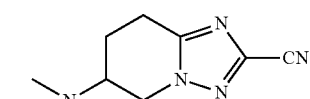

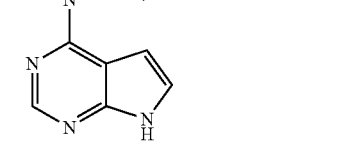

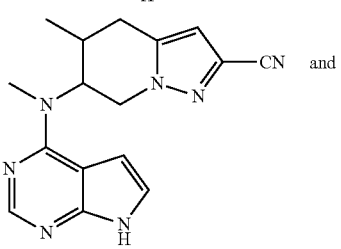

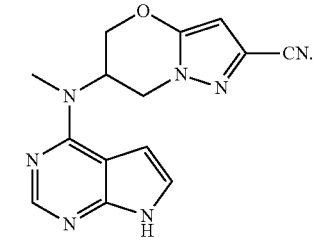

In some embodiments of the present invention, the compound, the isomer thereof or the pharmaceutically acceptable salt thereof is selected from:

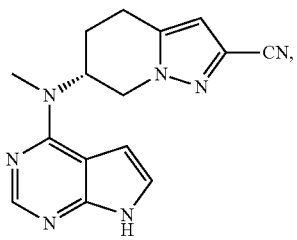

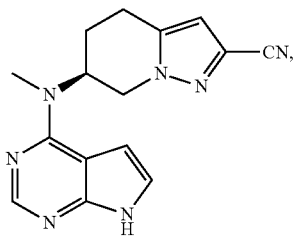

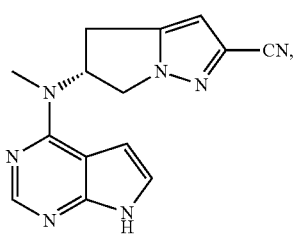

-continued

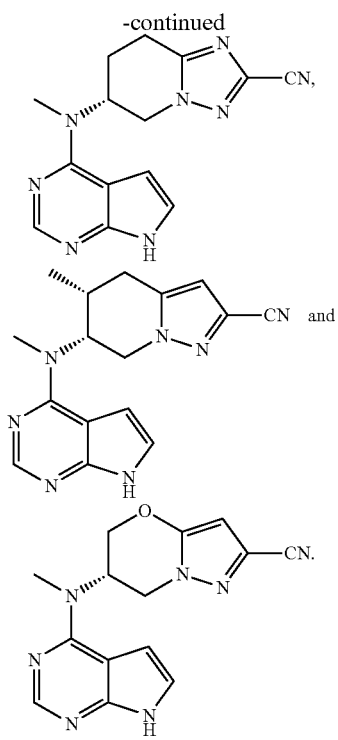

The present invention also provides use of the compound or the pharmaceutically acceptable salt thereof in preparing a medicament for treating a JAK1- or/and JAK2-related disease.

In still some other embodiments of the present invention, the medicament is a medicament for treating rheumatoid arthritis.

TECHNICAL EFFECTS

The compound disclosed herein exhibits good selective inhibition against JAK1 and/or JAK2 in in vitro activity assay of 4 kinase subtypes JAK1, JAK2, JAK3 and TYK2; the compound has good permeability, and is favorable for realizing desirable target tissue concentration and oral bioavailability; the compound disclosed herein has good oral bioavailability and high exposure in mice, and is beneficial for generating good in vivo efficacy.

DEFINITIONS AND DESCRIPTION

Unless otherwise stated, the following terms and phrases used herein are intended to have the following meanings. A particular term or phrase, unless otherwise specifically defined, should not be considered as uncertain or unclear, but construed according to its common meaning. When referring to a trade name, it is intended to refer to its corresponding commercial product or its active ingredient.

The term "pharmaceutically acceptable" is used herein for those compounds, materials, compositions, and/or dosage forms which are, within the scope of sound medical judgment, suitable for use in contact with the tissues of human beings and animals without excessive toxicity, irritation, allergic response, or other problems or complications, and commensurate with a reasonable benefit/risk ratio.

The term "pharmaceutically acceptable salt" refers to a salt of the compound disclosed herein, which is prepared from the compound having particular substituents disclosed herein and a relatively nontoxic acid or base. When the compound disclosed herein contains a relatively acidic functional group, a base addition salt can be obtained by contacting such a compound with a sufficient amount of a base in a pure solution or a suitable inert solvent. Pharmaceutically acceptable base addition salts include sodium, potassium, calcium, ammonium, organic amine, or magnesium salts, or similar salts. When the compound disclosed herein contains a relatively basic functional group, an acid addition salt can be obtained by contacting such a compound with a sufficient amount of an acid in a pure solution or a suitable inert solvent. Examples of pharmaceutically acceptable acid addition salts include salts derived from inorganic acids, such as hydrochloric acid, hydrobromic acid, nitric acid, carbonic acid, bicarbonate radical, phosphoric acid, monohydrogen phosphate, dihydrogen phosphate, sulfuric acid, hydrogen sulfate, hydroiodic acid and phosphorous acid; and salts derived from organic acids, such as acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid and methanesulfonic acid. Also included are salts of amino acids (e.g., arginine) and salts of organic acids such as glucuronic acid. Certain specific compounds disclosed herein contain both basic and acidic functional groups that allow the compounds to be converted into either base or acid addition salts.

The pharmaceutically acceptable salts disclosed herein can be synthesized from a parent compound having an acidic or basic group by conventional chemical methods. In general, such salts are prepared by the following method: performing a reaction of the free acid or base form of the compound and a stoichiometric amount of an appropriate base or acid in water or an organic solvent or a mixture thereof.

The compound disclosed herein may have a specific geometric or stereoisomeric form. All such compounds are contemplated herein, including cis and trans isomers, (-)- and (+)-enantiomers, (R)- and (S)-enantiomers, diastereoisomers, (D)-isomers, (L)-isomers, and racemic mixtures and other mixtures thereof, such as an enantiomer or diastereomer enriched mixture, all of which are encompassed within the scope of the present invention. Substituents such as alkyl may have an additional asymmetric carbon atom. All these isomers and mixtures thereof are encompassed within the scope of the present invention.

Unless otherwise stated, the term "enantiomer" or "optical isomer" refers to stereoisomers that are mirror images of each other.

Unless otherwise stated, the term "cis-trans isomer" or "geometric isomer" results from the inability of a single bond of a ring carbon atom or a double bond to rotate freely.

Unless otherwise stated, the term "diastereoisomer" refers to stereoisomers in which molecules each have two or more chiral centers and are not mirror images of each other.

Unless otherwise stated, "(+)" stands for dextrorotation, "(-)" stands for levorotation, and "(±)" stands for racemization.

Unless otherwise stated, the absolute configuration of a stereogenic center is represented by a wedged solid bond (⌿) and a wedged dashed bond (⌿), and the relative configuration of a stereogenic center is represented by a straight solid bond (⌿) and a straight dashed bond (⌿). A wavy line (⌿) represents a wedged solid bond (⌿) or a wedged dashed bond ( ) or a wavy line ( ) represents a straight solid bond ( ) and a straight dashed bond ( ).

Unless otherwise stated, when a double bond structure such as a carbon-carbon double bond, a carbon-nitrogen double bond, and a nitrogen-nitrogen double bond is present in the compound, and each atom on the double bond is linked to two different substituents (in the double bond including an nitrogen atom, a lone pair of electrons on the nitrogen atom is regarded as a substituent to which the nitrogen atom is linked), if the atom on the double bond of the compound and its substituents are linked using a wavy line ( ), it means that the compound exists in the form of a (Z)-type isomer, an (E)-type isomer, or a mixture of the two isomers. For example, the following formula (A) represents that the compound exists in the form of a single isomer of formula (A-1) or formula (A-2) or in the form of a mixture of both isomers of formula (A-1) and formula (A-2); the following formula (B) represents that the compound exists in the form of a single isomer of formula (B-1) or formula (B-2) or in the form of a mixture of both isomers of formula (B-1) and formula (B-2); and the following formula (C) represents that the compound exists in the form of a single isomer of formula (C-1) or formula (C-2) or in the form of a mixture of both isomers of formula (C-1) and formula (C-2).

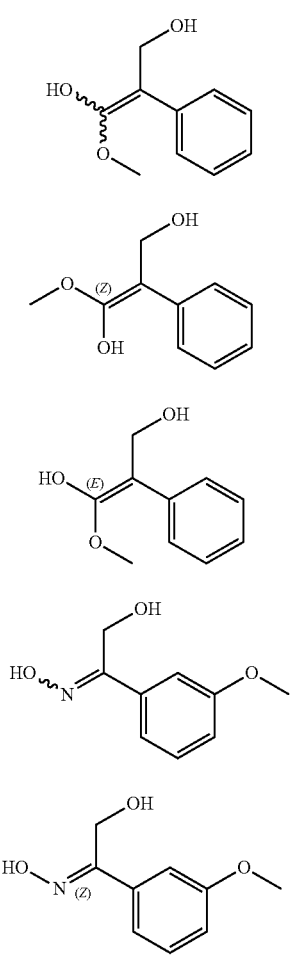

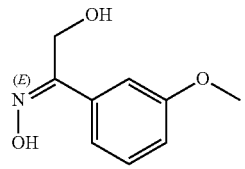

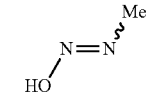

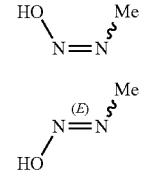

Unless otherwise stated, the term "tautomer" or "tautomeric form" means that different functional isomers are in dynamic equilibrium at room temperature and can be rapidly converted into each other. If tautomers are possible (e.g., in solution), the chemical equilibrium of the tautomers can be achieved. For example, a proton tautomer, also known as a prototropic tautomer, includes interconversion by proton migration, such as keto-enol isomerism and imine-enamine isomerism. A valence isomer includes interconversion by recombination of some bonding electrons. A specific example of the keto-enol tautomerism is the interconversion between the tautomers pentane-2,4-dione and 4-hydroxypent-3-en-2-one.

Unless otherwise stated, the term "enriched with one isomer", "isomer enriched", "enriched with one enantiomer", or "enantiomer enriched" means that the content of one of the isomers or enantiomers is less than 100% and more than or equal to 60%, 70%, 80%, 90%, 95%, 96%, 97%, 98%, 99%, 99.5%, 99.6%, 99.7%, 99.8%, or 99.9%.

Unless otherwise stated, the term "isomeric excess" or "enantiomeric excess" refers to the difference between the relative percentages of two isomers or enantiomers. For example, if the content of one isomer or enantiomer is 90% and the content of the other isomer or enantiomer is 10%, the isomeric or enantiomeric excess (ee) is 80%.

Optically active (R)- and (S)-isomers and D and L isomers can be prepared by chiral synthesis or chiral reagents or other conventional techniques. If one enantiomer of a certain compound disclosed herein is to be obtained, the desired pure enantiomer can be prepared by asymmetric synthesis or derivatization using a chiral auxiliary, wherein the resulting diastereoisomeric mixture is separated and the auxiliary group is cleaved. Alternatively, when the molecule contains a basic functional group (such as amino) or an acidic functional group (such as carboxyl), the compound reacts with an appropriate optically active acid or base to form a salt of the diastereoisomer, which is then subjected to diastereoisomeric resolution through conventional methods in the art to get the pure enantiomer. Furthermore, the enantiomer and the diastereoisomer are generally isolated through chromatography using a chiral stationary phase, optionally in combination with chemical derivatization (e.g., carbamate generated from amines).

The compound disclosed herein may contain an unnatural proportion of atomic isotope at one or more of the atoms that constitute the compound. For example, the compound may be labeled with a radioisotope, such as tritium ($^3$H), iodine-125 ($^{125}$I) or C-14 ($^{14}$C). For another example, hydrogen can be substituted by deuterium to form a deuterated drug, and the bond formed by deuterium and carbon is firmer than that formed by common hydrogen and carbon. Compared with an un-deuterated drug, the deuterated drug has the advantages of reduced toxic side effect, increased stability, enhanced efficacy, prolonged biological half-life and the like. All isotopic variations of the compounds disclosed herein, whether radioactive or not, are encompassed within the scope of the present invention. "Optional" or "optionally" means that the subsequently described event or circumstance may, but does not necessarily, occur, and the description includes instances where the event or circumstance occurs and instances where it does not.

The term "substituted" means that one or more hydrogen atoms on a specific atom are substituted by substituents which may include deuterium and hydrogen variants, as long as the valence of the specific atom is normal and the substituted compound is stable. When the substituent is an oxygen (i.e., =O), it means that two hydrogen atoms are substituted. Substitution with oxygen does not occur on aromatic groups. The term "optionally substituted" means that an atom can be substituted with a substituent or not. Unless otherwise specified, the type and number of the substituent may be arbitrary as long as being chemically achievable.

When any variable (e.g., R) occurs more than once in the constitution or structure of a compound, the variable is independently defined in each case. Thus, for example, if a group is substituted with 0-2 R, the group can be optionally substituted with up to two R, and the definition of R in each case is independent. Furthermore, a combination of a substituent and/or a variant thereof is permissible only if the combination can result in a stable compound.

When the number of a linking group is 0, for example, —(CRR)$_0$—, it means that the linking group is a single bond.

When one of variants is selected from single bond, then two groups bonding by this variant are bonded directly. For example, in A-L-Z, when L represents a single bond, it means that the structure is actually A-Z.

When a substituent is absent, it means that the substituent does not exist. For example, when X in A-X is absent, the structure is actually A. When it is not specified by which atom the listed substituent is connected to the group to be substituted, the substituent can be connected via any atom of the group. For example, pyridinyl as a substituent can be connected to the group to be substituted via any carbon atom on the pyridine ring.

Unless otherwise specified, when a group has one or more connectable sites, any one or more of the sites of the group may be connected to other groups by chemical bonds. When there is no designated connecting mode for a chemical bond and H atoms are present at a connectable site, the number of the H atoms at the connectable site is correspondingly reduced based on the number of the connected chemical bonds, and a group with a corresponding valence number is thus formed. The chemical bond that connects the site to another group may be represented by a straight solid bond (╱), a straight dashed line bond (╱), or a wavy line

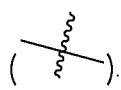

For example, the straight solid bond in —OCH$_3$ refers to being connected to another group via the oxygen atom in the group; the straight dashed bond in

refers to being connected to another group via two ends of the nitrogen atom in the group; the wavy line in

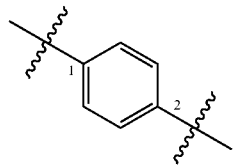 [SMILES: *c1ccc(*)cc1]

refers to being connected to another group via the carbon atoms at positions 1 and 2 in the phenyl group;

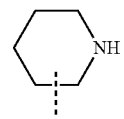

means that any connectable site on the piperidinyl can be connected to another group via 1 bond, and at least 4 connecting modes

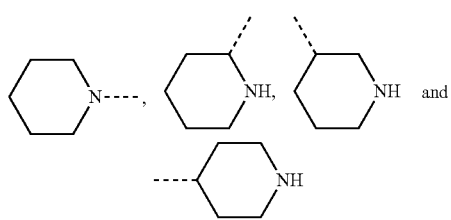

are possible; even if —N— is connected to an H atom,

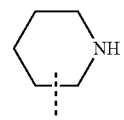

includes the connecting mode of

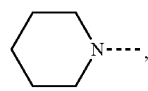

except that when 1 bond is connected to a site, the number of H at that site is correspondingly reduced by 1 and a monovalent piperidinyl is thus formed.

Unless otherwise specified, the term "C$_{1-3}$ alkyl" refers to a linear or branched saturated hydrocarbon group consisting of 1 to 3 carbon atoms. C$_{1-3}$ alkyl includes, but is not limited to, C$_{1-2}$ and C$_{2-3}$ alkyl, etc., and may be monovalent (e.g., methyl), divalent (e.g., methylene), or polyvalent (e.g., methenyl). Examples of $C_{1-3}$ alkyl include, but are not limited to, methyl (Me), ethyl (Et), and propyl (including n-propyl and isopropyl).

Unless otherwise specified, the term "halo" or "halogen", by itself or as part of another substituent, refers to a fluorine, chlorine, bromine or iodine atom.

Unless otherwise specified, $C_{n-n+m}$ or $C_n-C_{n+m}$ includes any one of the specific cases of n to n+m carbon atoms. For example, $C_{1-12}$ includes $C_1$, $C_2$, $C_3$, $C_4$, $C_5$, $C_6$, $C_7$, $C_8$, $C_9$, $C_{10}$, $C_{11}$ and $C_{12}$. Also, any range within n to n+m may be included. For example, $C_{1-12}$ includes $C_{1-3}$, $C_{1-6}$, $C_{1-9}$, $C_{3-6}$, $C_{3-9}$, $C_{3-12}$, $C_{6-9}$, $C_{6-12}$ and $C_{9-12}$. Similarly, n–n+m membered represents that the number of atoms on the ring is n to n+m. For example, 3-12 membered ring includes 3 membered ring, 4 membered ring, 5 membered ring, 6 membered ring, 7 membered ring, 8 membered ring, 9 membered ring, 10 membered ring, 11 membered ring and 12 membered ring. n–n+m membered also represents any range within n to n+m. For example, 3-12 membered ring includes 3-6 membered ring, 3-9 membered ring, 5-6 membered ring, 5-7 membered ring, 6-7 membered ring, 6-8 membered ring, and 6-10 membered ring.

The term "leaving group" refers to a functional group or atom that can be replaced by another functional group or atom through a substitution reaction (e.g., nucleophilic substitution). For example, representative leaving groups include triflate; chlorine, bromine and iodine; sulfonate groups, such as mesylate, tosylate, p-bromobenzenesulfonate, and p-toluenesulfonate; and acyloxy groups, such as acetoxy and trifluoroacetoxy.

The term "protecting group" includes, but is not limited to, "amino protecting group", "hydroxy protecting group" or "sulfydryl protecting group". The term "amino protecting group" refers to a protecting group suitable for preventing side reactions at the nitrogen atom of the amino. Representative amino protecting groups include, but are not limited to: formyl; acyl, such as alkanoyl (such as acetyl, trichloroacetyl or trifluoroacetyl); alkoxycarbonyl, such as t-butoxycarbonyl (Boc); arylmethyloxycarbonyl, such as benzyloxycarbonyl (Cbz) and 9-fluorenylmethyloxycarbonyl (Fmoc); arylmethyl, such as benzyl (Bn), trityl (Tr), 1,1-di-(4'-methoxyphenyl)methyl; and silyl, such as trimethylsilyl (TMS) and t-butyldimethylsilyl (TB S). The term "hydroxy protecting group" refers to a protecting group suitable for preventing side reactions of the hydroxyl group. Representative hydroxy protecting groups include, but are not limited to: alkyl, such as methyl, ethyl, and t-butyl; acyl, such as alkanoyl (such as acetyl); arylmethyl, such as benzyl (Bn), p-methoxybenzyl (PMB), 9-fluorenylmethyl (Fm) and diphenylmethyl (DPM); and silyl, such as trimethylsilyl (TMS) and t-butyldimethylsilyl (TBS).

The compounds of the present invention can be prepared by a variety of synthetic methods well known to those skilled in the art, including the specific embodiments listed below, embodiments formed by combinations thereof with other chemical synthetic methods, and equivalents thereof known to those skilled in the art. Preferred embodiments include, but are not limited to, the examples disclosed herein.

The solvent used herein can be commercially available. The following abbreviations are used herein: aq represents aqueous; DMF represents N,N-dimethylformamide.

DETAILED DESCRIPTION OF THE PREFERRED EMBODIMENT

The present invention is described in detail below by way of examples. However, this is by no means disadvantageously limiting the scope of the present invention. Although the present invention has been described in detail herein and specific examples have also been disclosed, it will be apparent to those skilled in the art that various changes and modifications can be made to the specific examples without departing from the spirit and scope of the present invention.

Example 1: Synthesis of Compound 1-13

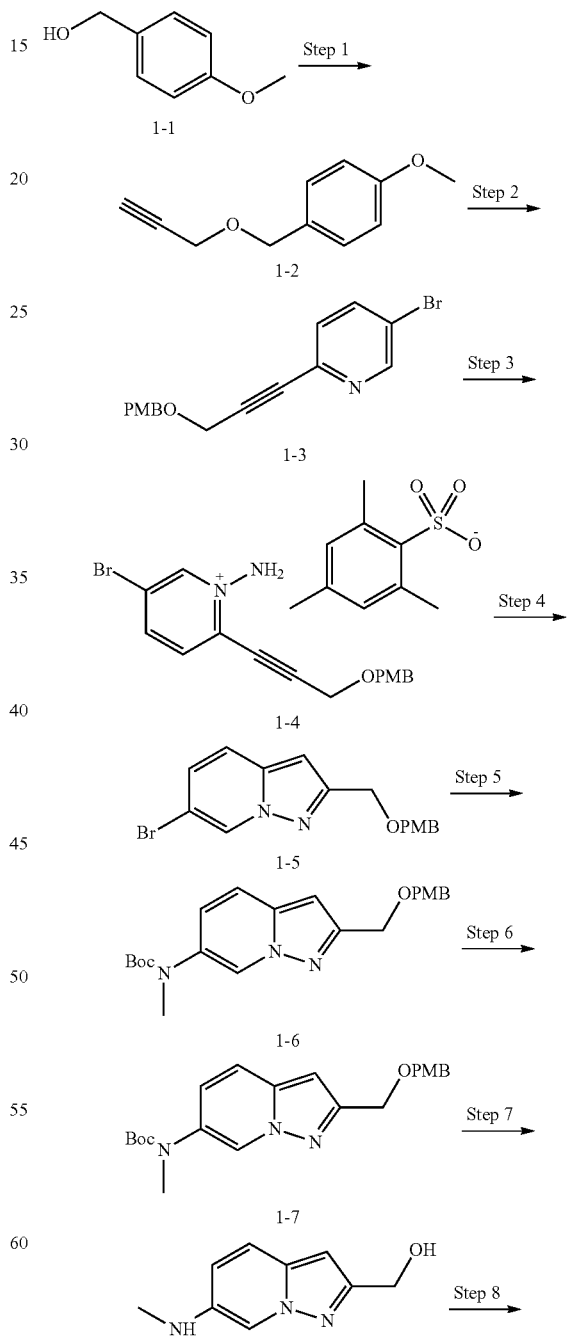

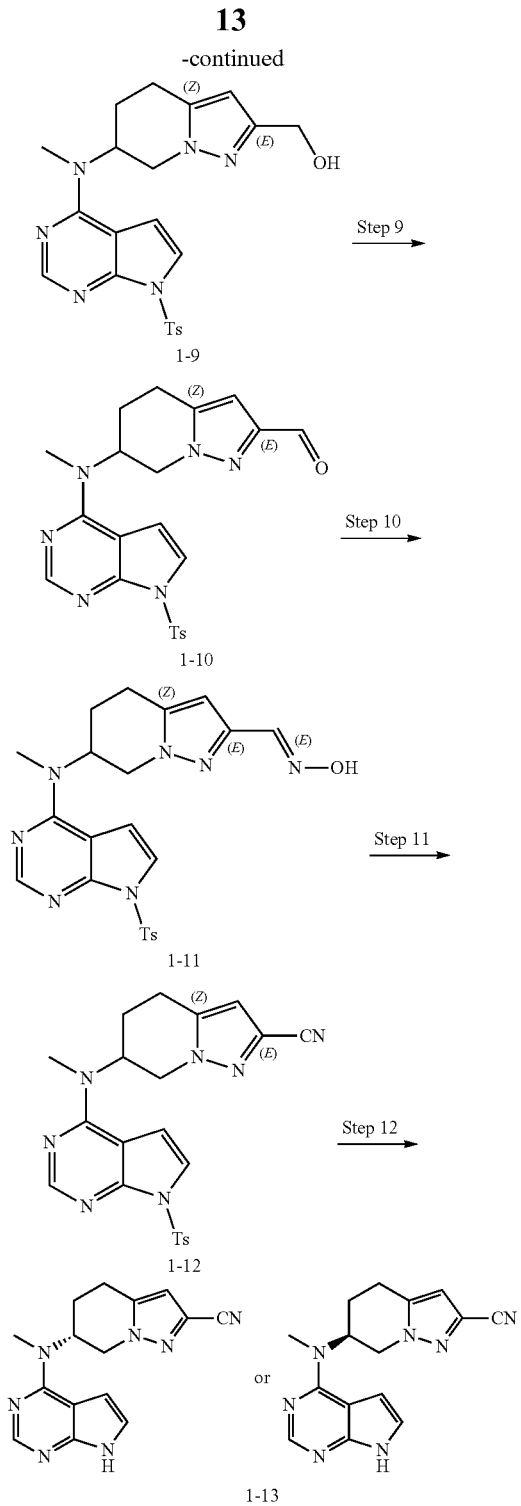

Step 1: (4-Methoxyphenyl)methanol (50 g, 361.89 mmol, 45.05 mL, 1 eq) was added to a suspension of sodium hydride (15.92 g, 398.08 mmol, 60% purity, 1.1 eq) in DMF (500 mL) at 0° C. The reaction mixture was stirring for 0.5 h before 3-bromoprop-1-yne (59.19 g, 398.08 mmol, 42.89 mL, 1.1 eq) was added slowly. The resulting solution was stirred at 0° C. for 2.5 h and at 25° C. for 16 h. TLC (PE:EA=10:1) showed that the reaction was completed and a new main product was formed. Saturated aqueous ammonium chloride (500 mL) was added to the reaction. The aqueous phase was extracted with ethyl acetate (500 m×3). The combined organic phases were washed with water (200 mL×2) and brine (200 mL×1), dried over anhydrous sodium sulfate, filtered and concentrated at reduced pressure. The resulting residue was purified by column chromatography (petroleum ether/ethyl acetate=1/0-1/1) to obtain compound 1-2. $^1$H NMR (400 MHz, DMSO-$d_6$) δ=7.27-7.22 (m, 2H), 6.93-6.89 (m, 2H), 4.44 (s, 1H), 4.46-4.41 (m, 1H), 4.12 (d, J=2.4 Hz, 2H), 3.74 (s, 2H), 3.77-3.72 (m, 1H), 3.46 (t, J=2.4 Hz, 1H), 3.48-3.45 (m, 1H), 3.48-3.45 (m, 1H), 3.48-3.45 (m, 1H), 3.48-3.44 (m, 1H).

Step 2: Compound 1-2 (34.14 g, 193.74 mmol, 25.00 mL, 1.1 eq), cuprous iodide (3.35 g, 17.61 mmol, 0.1 eq), piperidine (44.99 g, 528.37 mmol, 52.18 mL, 3 eq) and bis(triphenylphosphine)palladium(II) dichloride (6.18 g, 8.81 mmol, 0.05 eq) were added to a solution of 5-bromo-2-iodo-pyridine (50 g, 176.12 mmol, 1 eq) in THF (500 mL) at 25° C. The reaction system was purged with nitrogen three times, and the resulting solution was stirred at 25° C. for 16 h. TLC (PE:EA=10:1) showed that the reaction was completed and a new main product was formed. The reaction solution was filtered through celite and the filtrate was concentrated at reduced pressure. The residue was dissolved in 800 mL of ethyl acetate, and sequentially washed with 300 mL of water and 300 mL of brine. The organic phase was dried over anhydrous sodium sulfate, filtered and concentrated at reduced pressure. The residue was purified by column chromatography (silica, petroleum ether/ethyl acetate=1/0-30/1) to obtain compound 1-3. $^1$H NMR (400 MHz, CDCl$_3$-d) δ=8.61 (d, J=1.8 Hz, 1H), 7.75 (dd, J=2.4, 8.4 Hz, 1H), 7.32-7.28 (m, 1H), 7.32-7.26 (m, 1H), 7.27 (s, 1H), 6.89-6.84 (m, 2H), 4.58 (s, 2H), 4.35 (s, 2H), 3.79-3.76 (m, 1H), 3.77 (s, 2H).

Step 3: was added to compound 1-3 (1 g, 3.01 mmol, 1 eq) at 0° C., and the resulting solution was stirred for 16 h at 25° C. TLC (PE:EA=2:1) showed a small amount of starting material remained and a new main product was formed. 32 mL of t-butyl methyl ether was slowly added to the reaction system with stirring at 0° C. A large amount of off-white solid was slowly precipitated. The mixture was filtered and dried to obtain compound 1-4. $^1$H NMR (400 MHz, CHLOROFORM-d) δ=9.68-9.61 (m, 1H), 7.87-7.79 (m, 1H), 7.45-7.40 (m, 1H), 7.22-7.19 (m, 2H), 6.85-6.77 (m, 2H), 6.76-6.69 (m, 2H), 4.51-4.44 (m, 2H), 4.40-4.32 (m, 2H), 3.78-3.71 (m, 3H), 2.64-2.58 (m, 6H), 2.18-2.13 (m, 3H).

Step 4: Silver carbonate (10.07 g, 36.53 mmol, 1.66 mL, 2 eq) was added to a solution of compound 1-4 (10 g, 18.27 mmol, 1 eq) in DMF (160 mL) at 25° C. The resulting solution was stirred at 40° C. for 16 h. LCMS showed that the reaction was completed and a new main product was formed. The reaction solution was filtered through celite and the filtrate was concentrated at reduced pressure. The residue was dissolved in 200 mL of ethyl acetate, and sequentially washed with 100 mL of water and 100 mL of brine. The organic phase was dried over anhydrous sodium sulfate, filtered and concentrated at reduced pressure. The residue was purified by column chromatography (silica, petroleum ether/ethyl acetate=1/0-5/1) to obtain compound 1-5. $^1$H NMR (400 MHz, CDCl$_3$-d) δ=8.50-8.46 (m, 1H), 8.50-8.46 (m, 1H), 7.34-7.27 (m, 1H), 7.26-7.21 (m, 2H), 7.10-7.06 (m, 1H), 6.84-6.78 (m, 2H), 6.50-6.46 (m, 1H), 4.67-4.60 (m, 2H), 4.51-4.46 (m, 2H), 3.75-3.71 (m, 3H).

Step 5: Cesium carbonate (8.82 g, 27.07 mmol, 2 eq), 4,5-bis(diphenylphosphino)-9,9-dimethylxanthene (783.26 mg, 1.35 mmol, 0.1 eq) and tris(dibenzylideneacetone) dipalladium (619.79 mg, 676.83 µmol, 0.05 eq) were sequentially added to a solution of compound 1-5 (4.7 g, 13.54 mmol, 1 eq) and t-butyl N-methylcarbamate (5.33 g, 40.61 mmol, 3 eq) in DME (30 mL) at 25° C. The reaction system was purged with nitrogen three times. The resulting solution was stirred at 100° C. for 16 h. LCMS showed that the reaction was completed and a new main product was formed. The reaction solution was filtered through celite, and the filter cake was washed with 100 mL of ethyl acetate. The combined organic phases were washed sequentially with 100 mL of water and 100 mL of brine, dried over anhydrous sodium sulfate, filtered, and concentrated at reduced pressure. The residue was purified by column chromatography (silica, petroleum ether/ethyl acetate=1/0-20/1) to obtain compound 1-6. By MS (ESI), the calculation value of $C_{22}H_{27}N_3O_4$ was 397, and measurement value was 398 $[M+H]^+$.

Step 6: Platinum dioxide (933.33 mg, 4.11 mmol, 4.08e-1 eq) was added to a solution of compounds 1-6 (4 g, 10.06 mmol, 1 eq) in EtOH (60 mL) in nitrogen atmosphere at 25° C. The reaction system was purged with $H_2$ three times. The resulting solution was stirred in $H_2$ atmosphere at 70° C. (3 MPa) for 72 h. LCMS showed that the reaction was completed and a new main product was formed. The reaction solution was filtered through celite, and the filtrate was concentrated at reduced pressure to obtain compound 1-7. By MS (ESI), the calculation value of $C_{22}H_{31}N_3O_4$ was 401, and measurement value was 402 $[M+H]^+$; $^1H$ NMR (400 MHz, $CDCl_3$-d) δ=7.32-7.27 (m, 2H), 6.91-6.85 (m, 2H), 6.07-5.98 (m, 1H), 4.53-4.50 (m, 2H), 4.49-4.46 (m, 2H), 4.32-4.24 (m, 1H), 4.00-3.90 (m, 1H), 3.82-3.79 (m, 3H), 3.82-3.78 (m, 3H), 3.84-3.78 (m, 3H), 3.04-2.93 (m, 1H), 2.88-2.82 (m, 3H), 2.82-2.74 (m, 1H), 2.05-1.89 (m, 2H), 1.52-1.46 (m, 9H), 1.50-1.45 (m, 9H), 1.43-1.35 (m, 1H).

Step 7: Trifluoroacetic acid (12.33 g, 108.10 mmol, 8.00 mL, 10.85 eq) was added to a solution of compound 1-7 (4 g, 9.96 mmol, 1 eq) in DCM (40 mL) at 0° C. The resulting solution was stirred at 25° C. for 2 h. LCMS showed that the reaction was completed and a new main product was formed. The solution was concentrated at reduced pressure to obtain compound 1-8. By MS (ESI), the calculation value of $C_9H_{15}N_3O$ was 181, and measurement value was 182 $[M+H]^+$.

Step 8: N,N-diisopropylethylamine (9.56 g, 74.00 mmol, 12.89 mL, 7.85 eq) was added to a solution of 4-chloro-7-(p-toluenesulfonyl)pyrrolo[2,3-d]pyrimidine (2.9 g, 9.42 mmol, 1 eq) and compound 1-8 (1.81 g, 9.99 mmol, 1.06 eq) in DMSO (10 mL) at 25° C. The resulting solution was stirred at 110° C. for 16 h. LCMS showed that the reaction was completed and a new main product was formed. The reaction solution was slowly added to 50 mL of water and a light brown solid was precipitated slowly. The mixture was filtered and dried to obtain compound 1-9. By MS (ESI), the calculation value of $C_{22}H_{24}N_6O_3S$ was 452, and measurement value was 453 $[M+H]^+$; $^1H$ NMR (400 MHz, DMSO-$d_6$) δ=8.30-8.24 (m, 1H), 8.01-7.95 (m, 2H), 7.66-7.62 (m, 1H), 7.47-7.40 (m, 2H), 6.99-6.93 (m, 1H), 5.99-5.94 (m, 1H), 5.33-5.17 (m, 1H), 4.96-4.89 (m, 1H), 4.37-4.31 (m, 2H), 4.19-4.11 (m, 1H), 4.10-3.99 (m, 1H), 3.27-3.22 (m, 3H), 3.00-2.90 (m, 1H), 2.87-2.75 (m, 1H), 2.39-2.34 (m, 3H), 2.21-2.10 (m, 1H), 2.00-1.90 (m, 1H).

Step 9: Manganese dioxide (5.76 g, 66.29 mmol, 15 eq) was added to a solution of compound 1-9 (2 g, 4.42 mmol, 1 eq) in a mixed solvent of DCM (20 mL) and MeOH (2 mL) at 25° C. The resulting solution was stirred at 65° C. for 16 h. LCMS showed that the reaction was completed and a new main product was formed. The reaction solution was filtered through celite, and the filtrate was concentrated at reduced pressure to obtain compound 1-10. By MS (ESI), the calculation value of $C_{22}H_{22}N_6O_3S$ was 450, and measurement value was 451 $[M+H]^+$.

Step 10: A solution of hydroxylamine hydrochloride (370.19 mg, 5.33 mmol, 1.2 eq) and sodium acetate (509.83 mg, 6.22 mmol, 1.4 eq) in $H_2O$ (5 mL) was added to a solution of compound 1-10 (2 g, 4.44 mmol, 1 eq) in EtOH (15 mL) at 25° C. The resulting solution was stirred at 25° C. for 0.5 h and at 80° C. for 1.5 h. LCMS showed that the reaction was completed and a new main product was formed. The reaction solution was concentrated at reduced pressure. The residue was diluted with 50 mL and extracted with DCM (50 mL×3). The combined organic phases were washed with 100 mL of brine, dried over anhydrous sodium sulfate, filtered and concentrated at reduced pressure to obtain compound 1-11. By MS (ESI), the calculation value of $C_{22}H_{23}N_7O_3S$ was 465, and measurement value was 466 $[M+H]^+$.

Step 11: 2,4,6-Tripropyl-1,3,5,2,4,6-trioxatriphosphinane 2,4,6-trioxide (9.57 g, 15.04 mmol, 8.94 mL, 50% purity, 5 eq) was added to a solution of compound 1-11 (1.4 g, 3.01 mmol, 1 eq) in THF (15 mL) at 25° C. The system was stirred for 10 min before triethylamine (4.56 g, 45.11 mmol, 6.28 mL, 15 eq) was added. The resulting solution was stirred at 70° C. for 16 h. LCMS showed that the reaction was completed and a new main product was formed. Saturated aqueous ammonium chloride (50 mL) was added to the reaction solution. The aqueous phase was extracted with dichloromethane (100 mL×3), and the combined organic phases were dried over anhydrous sodium sulfate, filtered and concentrated at reduced pressure. The resulting residue was purified by column chromatography (petroleum ether/ethyl acetate=1/0-1/1) to obtain compound 1-12. $^1H$ NMR (400 MHz, $CDCl_3$-d) δ=8.41-8.35 (m, 1H), 8.09-8.04 (m, 2H), 7.53-7.49 (m, 1H), 7.53-7.48 (m, 1H), 7.32-7.28 (m, 2H), 6.71-6.65 (m, 1H), 6.45-6.40 (m, 1H), 5.59-5.48 (m, 1H), 4.53-4.46 (m, 1H), 4.09-4.00 (m, 1H), 3.32-3.28 (m, 3H), 3.13-3.06 (m, 1H), 2.97-2.85 (m, 1H), 2.41-2.37 (m, 3H), 2.19-2.10 (m, 2H).

Step 12: A solution of tetrabutylammonium fluoride in tetrahydrofuran (1 M, 19.31 mL, 3.2 eq) was added to a solution of compound 1-12 (2.7 g, 6.03 mmol, 1 eq) in THF (20 mL) at 25° C. The resulting solution was stirred at 65° C. for 16 h. LCMS showed that the reaction was completed and a new main product was formed. The reaction mixture was concentrated at reduced pressure to remove the solvent. The residue was adjusted to an alkaline pH by adding saturated aqueous sodium bicarbonate solution. The mixture was filtered and then subjected to chiral resolution (chiral column: Chiralcel OJ-3 50×4.6 mm I.D., 3 μm; mobile phase: phase A was supercritical $CO_2$ and B phase was MeOH (0.05% DEA); gradient: B in A from 5% to 40%; flow rate: 3 mL/min; wavelength: 220 nm; column temperature: 35° C.; back pressure: 100 bar) to obtain (R or S) compound 1-13 (retention time: 1.656 min). By MS (ESI), the calculation value of $C_{15}H_{15}N_7$ was 293, and measurement value was 294 $[M+H]^+$; $^1H$ NMR (400 MHz, DMSO-$d_6$) δ=12.80-12.56 (m, 1H), 8.43-8.32 (m, 1H), 7.49-7.38 (m, 1H), 7.01-6.88 (m, 1H), 6.88-6.74 (m, 1H), 5.31-5.17 (m, 1H), 4.52-4.36 (m, 2H), 3.45-3.41 (m, 3H), 3.13-3.04 (m, 1H), 3.01-2.91 (m, 1H), 2.38-2.29 (m, 1H), 2.17-2.09 (m, 1H).

Biological Activity Assay

Experimental Example 1: In Vitro Activity Assay of JAK1, JAK2, JAK3, TYK2 Kinases

Materials

Recombinant human JAK1, JAK2, JAK3 and TYK2 protease, and main instruments and reagents were provided by Eurofins, UK

Procedures

JAK2, JAK3 and TYK2 dilutions: 20 mM 3-(N-morpholino)propanesulfonic acid (MOPS), 1 mM EDTA, 0.01% Brij-35.5% glycerol, 0.1% β-mercaptoethanol, 1 mg/mL BSA; JAK1 dilution: 20 mM TRIS, 0.2 mM EDTA, 0.1% β-mercaptoethanol, 0.01% Brij-35.5% glycerol. All compounds were prepared in 100% DMSO and brought to 50 fold the final assay concentration. The test compounds were serially 3-fold diluted to 9 concentrations from 10 μM to 0.001 μM with DMSO content in the assay reaction being 2%. Working stock solutions of the compounds were added to the assay wells as the first component of the reaction, and then the remaining components were added according to the assay protocol detailed below.

JAK1(h) Enzymatic Reaction

JAK1(h) was incubated with 20 mM Tris/HCl pH 7.5, 0.2 mM EDTA, 500 μM MGEEPLYWSFPAKKK, 10 mM magnesium acetate and [γ-$^{33}$P]-ATP (activity and concentration were determined as required). The reaction was started by adding the Mg/ATP mixture and terminated by adding 0.5% phosphoric acid after 40 min of incubation at room temperature. 10 μL of the reaction mixture was then added dropwise on a P30 filter pad and washed three times with 0.425% phosphoric acid and once with methanol within 4 minutes, dried and analyzed using a scintillation counter.

JAK2(h) Enzymatic Reaction

JAK2(h) was incubated with 8 mM MOPS pH 7.0, 0.2 mM EDTA, 100 μM KTFCGTPEYLAPEVRREPRILSEE-EQEMFRDFDYIADWC, 10 mM magnesium acetate and [γ-$^{33}$P]-ATP (activity and concentration were determined as required). The reaction was started by adding the Mg/ATP mixture and terminated by adding 0.5% phosphoric acid after 40 min of incubation at room temperature. 10 μL of the reaction mixture was then added dropwise on a P30 filter pad and washed three times with 0.425% phosphoric acid and once with methanol within 4 minutes, dried and analyzed using a scintillation counter.

JAK3(h) Enzymatic Reaction

JAK3(h) was incubated with 8 mM MOPS pH 7.0, 0.2 mM EDTA, 500 μM GGEEEEYFELVKKKK, 10 mM magnesium acetate and [γ-$^{33}$P]-ATP (activity and concentration were determined as required). The reaction was started by adding the Mg/ATP mixture and terminated by adding 0.5% phosphoric acid after 40 min of incubation at room temperature. 10 μL of the reaction mixture was then added dropwise on a P30 filter pad and washed three times with 0.425% phosphoric acid and once with methanol within 4 minutes, dried and analyzed using a scintillation counter.

TYK2(h) Enzymatic Reaction

TYK2(h) was incubated with 8 mM MOPS pH 7.0, 0.2 mM EDTA, 250 μM GGMEDIYFEFMGGKKK, 10 mM magnesium acetate and [γ-$^{33}$P]-ATP (activity and concentration were determined as required). The reaction was started by adding the Mg/ATP mixture and terminated by adding 0.5% phosphoric acid after 40 min of incubation at room temperature. 10 μL of the reaction mixture was then added dropwise on a P30 filter pad and washed three times with 0.425% phosphoric acid and once with methanol within 4 minutes, dried and analyzed using a scintillation counter.

Data Analysis

The $IC_{50}$ results were obtained by XLFIT5 (formula 205) from IDBS corporation, as shown in Table 1.

TABLE 1

Results of in vitro screening for compounds disclosed herein

| Compounds | JAK1 ($IC_{50}$, nM) | JAK2 ($IC_{50}$, nM) | JAK3 ($IC_{50}$, nM) | TYK2 ($IC_{50}$, nM) |
|---|---|---|---|---|
| 1-13 | 1 | 8 | 118 | 15 |

Conclusion: The compounds disclosed herein exhibited good selective inhibition on JAK1 and/or JAK2 in the in vitro activity assay of the 4 kinase subtypes JAK1, JAK2, JAK3 and TYK2.

Experimental Example 2: Permeability Test

Materials

The transport buffer solution was HBSS (Hanks' balanced salt solution) and 10 mM HEPES [N-(2-hydroxyethyl)piperazine-N'-(2-ethanesulfonic acid)], pH 7.40±0.05; Caco-2 cells were purchased from ATCC.

Procedures

Caco-2 cells were seeded at 1×10$^5$ cells/cm$^2$ in polyethylene terephthalate (PET) 96-well BD insert plates, and the medium was refreshed every 4-5 days until day 21-28 to form a confluent monolayer. Test compounds were tested in a two-way format at 2 μM in duplicate. Digoxin was added at 10 μM in the two-way format, and nadolol and metoprolol were added at 2 μM in the two-way format. Final DMSO concentration was adjusted to less than 1%. The plates were incubated in a $CO_2$ incubator at 37±1° C. for 2 h and at 5% $CO_2$ and saturated humidity without shaking. All samples were mixed with acetonitrile containing an internal standard, centrifuged at 4000 rpm for 10 min. 100 microliters of supernatant was diluted with 100 microliters of distilled water for LC/MS/MS analysis. By LC/MS/MS analysis, the concentrations of the test compounds and the reference compound in the initial test compound solution, the test compound solution and the test article solution using the peak area ratio of the analyte to the internal standard. After the transport test, the integrity of the Caco-2 cell monolayer was determined by fluorescein yellow exclusion reaction, and the apparent permeability coefficient and efflux ratio were calculated.

Results

The experimental results are shown in Table 2-1:

TABLE 2-1

Permeability of compound 1-13

| Name | Mean apparent permeability coefficient Mean $P_{app}$ ($10^{-6}$ cm/s) | | Efflux ratio |
|---|---|---|---|
| | A to B | B to A | |
| Nadolol | 0.16 | ND | — |
| Metoprolol | 18.11 | ND | — |
| Digoxin | 0.04 | 13.88 | 349.25 |
| 1-13 | 28.58 | 31.18 | 1.09 |

Conclusion: the compound has characteristic high permeability, and is favorable for realizing good target tissue concentration and oral bioavailability.

Note: ND: not detectable.

Experimental Example 3: Pharmacokinetic (PK) Study

Clear solutions obtained by dissolving the test compounds were administered to male mice (C57BL/6) or rats (SD) by tail vein injection and oral gavage (overnight fasting, 7-8 weeks old). After the administration of the test compounds, plasma was separated from blood collected from the mandibular vein and centrifugation at 0.117, 0.333, 1, 2, 4, 7 and 24 h for the intravenous injection group (1 mg/kg), and at 0.25, 0.5, 1, 2, 4, 8 and 24 h for the oral gavage group (3 mg/kg). The plasma concentration was measured by LC-MS/MS method, and the relevant pharmacokinetic parameters were calculated by WinNonlin™ Version 6.3 pharmacokinetic software using non-compartmental model linear logarithmic trapezoid method. The test results are as follows:

TABLE 3-1

PK study results for compound 1-13 in mice

| PK parameters | Results |
|---|---|
| $T_{1/2}$ (hr) | 1.89 |
| $C_{max}$ (nM) | 6000 |
| $AUC_{0-inf}$ (nM · hr) | 12765 |
| Bioavailability (%)$^a$ | 88.4 |

Note:
$T_{1/2}$: half-life;
$C_{max}$: peak concentration;
$AUC_{0-inf}$: area under the plasma concentration-time curve from time 0 to infinity;
Bioavailability: bioavailability.

Conclusion: the compounds disclosed herein have good oral bioavailability and higher exposure in mice, and are favorable for producing good in-vivo efficacy.

Experimental Example 4: In-Vivo Pharmacodynamic Study of Adjuvant-Induced Arthritis (AIA) in Rats Procedures:
The compounds disclosed herein were tested for their efficacy on arthritis using a rat adjuvant-induced arthritis model. Female, 160- and 180-gram Lewis rats were anesthetized with isoflurane and injected subcutaneously with 0.1 mL of *Mycobacterium tuberculosis* suspension in the left hind paw. The animals were grouped and administered with the compounds 13 days after modeling. The rats were given different doses, as shown in Table 4-2. The test compound 1-13 was dissolved in a mixed vehicle of [5% DMSO, 95% (12% SBE-β-CD), 0.5% MC]. The female Lewis rats were orally administered 2 times daily (8 animals in each group). The status of the rats was observed for two weeks during which the swelling of the foot volume was recorded and scored with the criterion shown in Table 4-1.

TABLE 4-1

Clinical scoring criterion for arthritis

| Score | Symptoms |
|---|---|
| 0 | No erythema and redness |
| 1 | Erythema or mild redness near the tarsal bones or at the ankle joints or metatarsal bones, and redness or swelling in one toe |
| 2 | Slight erythema and redness of the ankle and metatarsal bones, or redness and erythema in two or more toes |
| 3 | Moderate erythema and swelling in the ankle, wrist, and metatarsals |
| 4 | Severe redness and swelling in the ankle, wrist, metatarsals and toes |

Results:
The two treatment groups of compound 1-13 showed significant relieving effect on the weight loss trend of animals caused by disease attack, and the low and medium dose groups (3 mg/kg and 10 mg/kg) showed significant difference since day 20 as compared to the solvent control group, suggesting good weight recovery effect. Compound 1-13 inhibited the increase in clinical arthritis score and paw volume, and this inhibition was dose-dependent. The effect of compound 1-13 10 mg/kg demonstrated the most significant efficacy (significant difference from the solvent control group starting from day 15). The mean clinical arthritis score for this group decreased from 6 points at day 13 to 1.4 points, the study endpoint, on day 27, and was significantly different as compared to the solvent control group.

TABLE 4-2

Inhibition on area under the clinical score curve (AUC)

| Compounds | Dosage (mg/kg) | AUC (%) |
|---|---|---|
| Vehicle control group | 0 | 0% |
| Compound 1-13 | 3 | 49.6 |
| | 10 | 60.5 |

Conclusion: compound 1-13 disclosed herein showed significant therapeutic effect (for the inhibition rate versus vehicle control P<0.0001) at doses 3 mg/kg and 10 mg/kg, and compound 1-13 disclosed herein showed positive correlation to the dose (3 mg/kg and 10 mg/kg).

What is claimed is:

1. A compound represented by formula (I), a stereoisomer thereof or a pharmaceutically acceptable salt thereof,

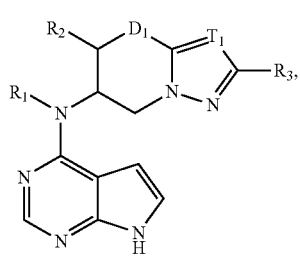
(I)

wherein, $T_1$ is CH;

$D_1$ is $CH_2$;

$R_1$ is H or $C_{1-3}$ alkyl, the $C_{1-3}$ alkyl is optionally substituted with 1, 2 or 3 $R_a$;

$R_2$ is H or $C_{1-3}$ alkyl, the $C_{1-3}$ alkyl is optionally substituted with 1, 2 or 3 $R_b$;

$R_3$ is selected from H, F, Cl, Br, I, CN and $C_{1-3}$ alkyl, the $C_{1-3}$ alkyl is optionally substituted with 1, 2 or 3 $R_c$;

$R_a$, $R_b$, and $R_c$ are each independently selected from F, Cl, Br, I and $NH_2$.

2. The compound, the stereoisomer thereof or the pharmaceutically acceptable salt thereof according to claim 1, wherein $R_1$ is H or $CH_3$.

3. The compound, the stereoisomer thereof or the pharmaceutically acceptable salt thereof according to claim 1, wherein $R_2$ is H or $CH_3$.

4. The compound, the stereoisomer thereof or the pharmaceutically acceptable salt thereof according to claim 1, wherein $R_3$ is selected from H, F, Cl, Br, I and CN.

5. The compound, the stereoisomer thereof or the pharmaceutically acceptable salt thereof according to claim 4, wherein $R_3$ is CN.

6. The compound, the stereoisomer thereof or the pharmaceutically acceptable salt thereof according to claim 1, which is selected from:

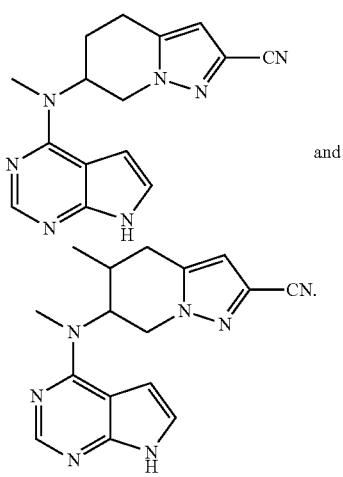

7. The compound, the stereoisomer thereof or the pharmaceutically acceptable salt thereof according to claim 6, which is selected from:

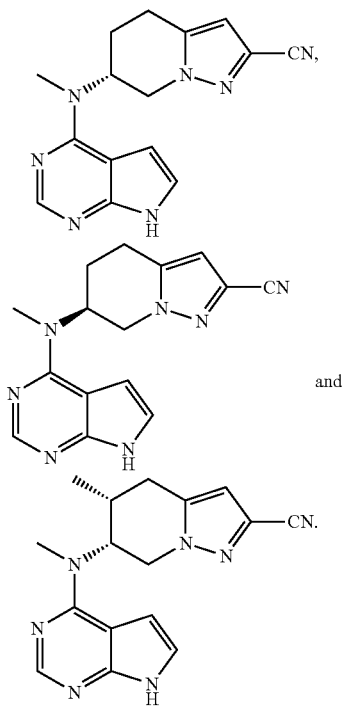

and

8. The compound, the stereoisomer thereof or the pharmaceutically acceptable salt thereof according to claim 1, wherein the compound is selected from:

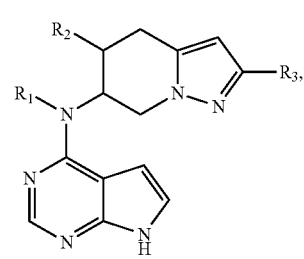
(I-1)

wherein $R_1$ is H or $CH_3$; $R_2$ is H or $CH_3$; and $R_3$ is selected from H, F, Cl, Br, I and CN.

9. The compound, the stereoisomer thereof or the pharmaceutically acceptable salt thereof according to claim 8, wherein the compound is selected from:

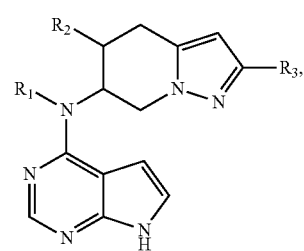
(I-1)

wherein $R_3$ is CN.

10. A method for treating a JAK1- or/and JAK2-related disease in a subject in need thereof, comprising administrating a therapeutically effective amount of the compound, the stereoisomer thereof or the pharmaceutically acceptable salt thereof according to claim 1.

11. The method according to claim 10, wherein the JAK1- or/and JAK2-related disease is rheumatoid arthritis.

12. A method for treating a JAK1- or/and JAK2-related disease in a subject in need thereof, comprising administrating a therapeutically effective amount of the compound, the stereoisomer thereof or the pharmaceutically acceptable salt thereof according to claim 7.

13. The method according to claim 12, wherein the JAK1- or/and JAK2-related disease is rheumatoid arthritis.

14. A method for treating a JAK1- or/and JAK2-related disease in a subject in need thereof, comprising administrating a therapeutically effective amount of the compound, the stereoisomer thereof or the pharmaceutically acceptable salt thereof according to claim 8.

15. The method according to claim 14, wherein the JAK1- or/and JAK2-related disease is rheumatoid arthritis.

16. A method for treating a JAK1- or/and JAK2-related disease in a subject in need thereof, comprising administrating a therapeutically effective amount of the compound, the stereoisomer thereof or the pharmaceutically acceptable salt thereof according to claim 11.

17. The method according to claim 16, wherein the JAK1- or/and JAK2-related disease is rheumatoid arthritis.

\* \* \* \* \*